(12) United States Patent
Pearce et al.

(10) Patent No.: US 8,308,482 B2
(45) Date of Patent: Nov. 13, 2012

(54) PERSONAL UNDER FIRE TRAINER FOR SECURITY AND MILITARY PERSONNEL

(75) Inventors: Timothy Andrew Pearce, Redondo Beach, CA (US); Jeffrey Frank Vasquez, Thousand Oaks, CA (US)

(73) Assignee: Timothy Andrew Pearce, Redondo Beach, CA (US)

( * ) Notice: Subject to any disclaimer, the term of this patent is extended or adjusted under 35 U.S.C. 154(b) by 249 days.

(21) Appl. No.: 12/881,259

(22) Filed: Sep. 14, 2010

(65) Prior Publication Data

US 2012/0064492 A1    Mar. 15, 2012

(51) Int. Cl.
*F41G 3/26*       (2006.01)
(52) U.S. Cl. ............................................. 434/11; 434/23
(58) Field of Classification Search .............. 434/11–26; 607/5–76; 473/212, 224; 482/148; 463/47.3; 361/232
See application file for complete search history.

(56) References Cited

U.S. PATENT DOCUMENTS

| 5,528,450 | A | * | 6/1996 | Willoughby et al. | ......... 361/232 |
| 5,815,077 | A | * | 9/1998 | Christiansen | ............... 340/573.3 |
| 2006/0121419 | A1 | | 6/2006 | Ferris et al. | |
| 2008/0001735 | A1 | * | 1/2008 | Tran | ........................ 340/539.22 |

OTHER PUBLICATIONS

Larry Greenemeier, "Video Game Vest Simulates Sensation of Being Capped", http://www.scientificamerican.com/article.cfm?video-game-vest-simulates, printed Feb. 13, 2011.

* cited by examiner

*Primary Examiner* — Timothy A Musselman
(74) *Attorney, Agent, or Firm* — John L. Rogitz

(57) ABSTRACT

A personal under fire trainer includes a harness holding a wireless receiver and plural electrode leads. The harness can be donned by a trainee and the leads connected to electrodes attached to the trainee's body. A trainer can operate a remote transmitter to send a signal to the receiver, activating one or more electrodes which contract the trainee's muscles, forcing the trainee to react under simulated gun fight conditions while receiving simulated gunshot wounds.

16 Claims, 4 Drawing Sheets receiver circuit receiver assembly

Figure 4 Kill Switch
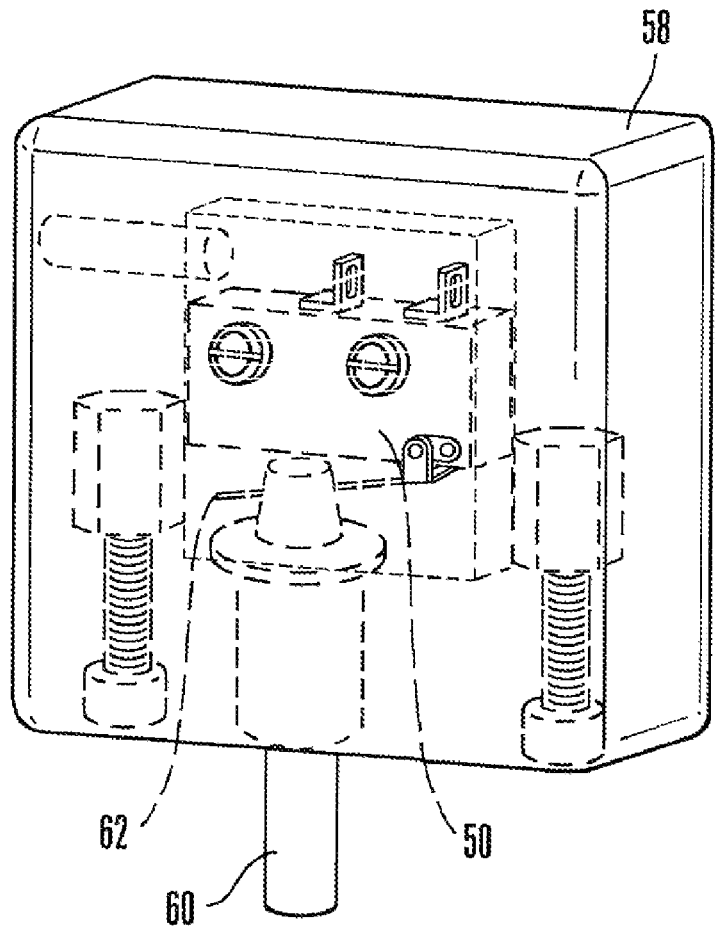
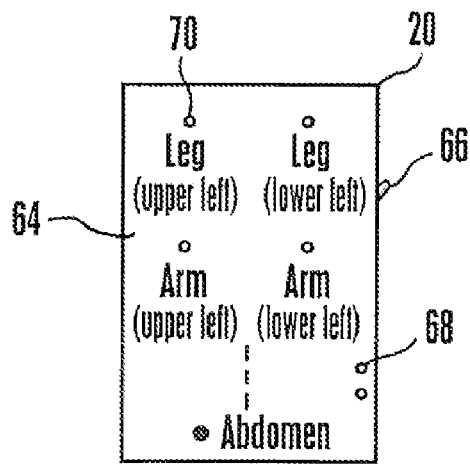
Figure 5
trainer transmitter

PERSONAL UNDER FIRE TRAINER FOR SECURITY AND MILITARY PERSONNEL

FIELD OF THE INVENTION

The present application relates generally to personal under fire trainers for security and military personnel.

BACKGROUND OF THE INVENTION

Police officers in training undergo a great many drills, one of which is practicing to cope during a simulated gun fight with simulated disabilities. Such drills are colloquially referred to as "Officer Down" scenarios. In such a training scenario a trainee might be positioned in a practice range or combat shooting course in which various targets move, with simulated shooting at the trainee being conducted. The purpose is to train an officer to return fire or otherwise cope with high stress circumstances during a gunfight.

As understood herein, a trainee simulating being hit by gunfire during an "Officer Down" exercise typically does so by pretending that his primary gun hand is rendered useless, tucking his primary gun hand in his belt and finishing the combat shooting course with his off-hand. As further recognized herein, simply returning fire during a drill using the off-hand is less than a realistic modeling of actual gun fight conditions, in which an officer might experience pain and trauma far beyond the inconvenience of tucking a hand in a belt.

SUMMARY OF THE INVENTION

Accordingly, an assembly is provided that can be worn by a trainee and operated remotely by a trainer to deliver a quick, powerful, yet safe muscle contraction to the trainee that temporarily immobilizes a portion of the trainee's body, similar to a gunshot wound. The gunshot simulator can be used to train public safety officers, military personnel, recreational participants in paintball contests, and the like to maintain accuracy and focus in combat shooting situations after being hit with an immobilizing simulated gunshot. The trainer can remotely target and contract any of the trainee's biceps, forearms, hamstrings, calves, or abdomen muscles to temporarily and safely incapacitate the targeted body section with a muscle contraction.

Thus, a training apparatus includes plural electrodes attachable to respective locations of a body of a patient and a harness wearable by the trainee and enveloping at least portions of the trainee's torso, shoulders, and upper thighs. One or more batteries are supported by the harness as is a wireless receiver assembly. A hand-held controller wirelessly communicates with the wireless receiver assembly and bears plural keys manipulable by a trainer to send activation signals to the wireless receiver assembly. The wireless receiver assembly, responsive to the activation signals, causes the battery to activate one or more of the electrodes and thereby cause contraction of at least one muscle of the trainee that is closely juxtaposed with the electrode activated by the battery to simulate a gunshot wound at the site of the electrode activated by the battery.

In some implementations, the wireless receiver assembly communicates with the electrodes through respective wires connected to respective electrodes. The wires are supported on the harness. Or, the wireless receiver assembly may wirelessly activate the electrodes. In non-limiting examples each electrode has a conductive gel center supported in a cloth body.

A trainee-actuated switch may be provided that is electrically disposed between the battery and at least one electrode and operable by the trainee to open an electrical circuit between the battery and electrode. This deactivates the electrode in the presence of an activation signal from the controller. Moreover, if desired a switch may be electrically disposed between the battery and at least one electrode and operable automatically to open an electrical circuit between the battery and electrode. This may be done responsive to a determination that the controller is deenergized or malfunctioning.

In another aspect, a method includes receiving, at a controller, trainer input of an activate command, and responsive to the trainer input, wirelessly sending an activate signal to a wireless receiver. Responsive to receiving the activate signal, the method includes causing the receiver to energize at least one electrode contacting a trainee's skin above a muscle to cause the muscle to contract. Also, responsive to receiving an emergency stop signal input by the trainee, the method includes deenergizing the electrode in the presence of the activate signal.

In another aspect, a personal under fire trainer includes a harness holding a wireless receiver assembly and plural electrode leads. The harness is wearable by a trainee with the leads connected to electrodes attached to the trainee's body. A controller is operable by a trainer to send a wireless signal to the receiver assembly, activating one or more electrodes which contract the trainee's muscles, forcing the trainee to react under simulated gun fight conditions while receiving simulated gunshot wounds.

The details of the present invention, both as to its structure and operation, can best be understood in reference to the accompanying drawings, in which like reference numerals refer to like parts, and in which:

BRIEF DESCRIPTION OF THE DRAWINGS

FIG. 4 is a perspective view of an example trainee-operated kill switch with the casing shown transparently; and FIG. 5 is a plan view of an example trainer remote control transmitter.

DETAILED DESCRIPTION OF THE PREFERRED EMBODIMENT

Figure 1:
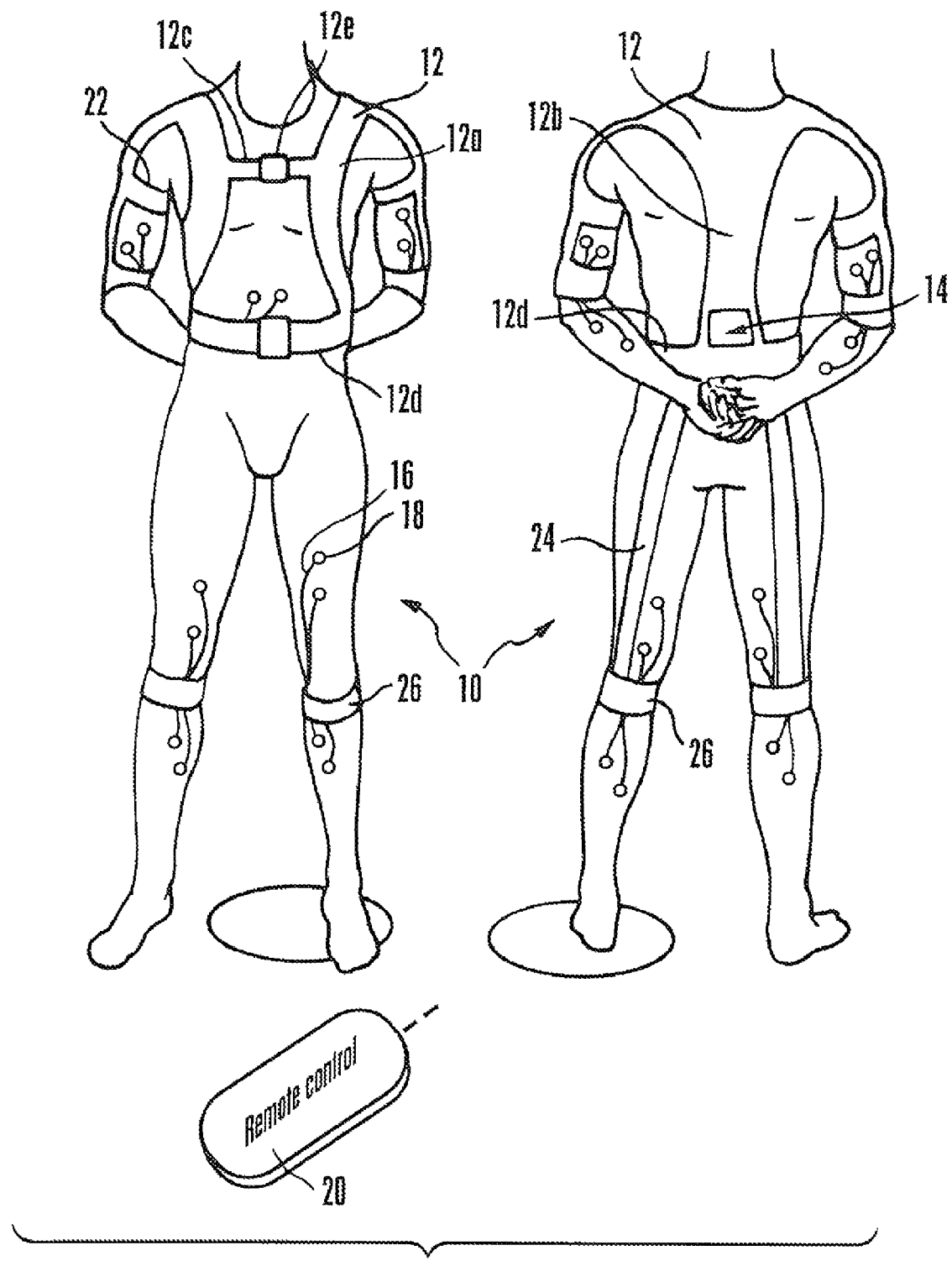
FIG. 1 is a schematic diagram of an example under fire system in accordance with present principles, showing the harness from both the front of the trainee and the rear of the trainee.

Referring initially to FIG. 1, an under fire training system is shown and generally designated 10. The system 10 includes a trainee-wearable harness 12 that bears a portable battery-powered receiver assembly 14. The harness 12, which can be made of nylon webbing, may be worn over a trainee's clothing and supports leads 16 which connect the receiver assembly 14 with plural electrical muscle stimulation (EMS) electrodes 18 which are selectively activated by the receiver assembly 14 responsive to trainer stimulation command signals received wirelessly from a transmitter remote control (RC) 20.

Accordingly, the harness 14 may be worn by a trainee and is triggered remotely by a trainer manipulating the RC 20. When activated, the electrodes 18 produce a strong muscle contraction on a targeted area on the trainee's body (e.g., arms, legs or abdomen). The resulting muscle contraction causes an extreme distraction, discomfort and immobilization of the targeted limb, thus simulating a life-like gunshot wound. In this way, the trainee completes various training scenarios while training himself to re-gain focus in the midst of a significant physical distraction so that he/she may return fire at a simulated advancing shooting suspect with accuracy despite the surprise, stress, and immobilization of the simulated gun shot wound.

The possible training scenarios for the system 10 are many. An example of one such scenario is a building search for an armed suspect. As the officer makes entry into the building, the suspect at some point approaches and engages the officer in simulated gunfire. Subsequently, the instructor remotely triggers the electrodes, which initiates a strong muscle contraction on the officer's forearm of his gun hand causing the officer to involuntarily open his hand and drop his weapon. The officer's forearm muscles will remain tightly contracted and immobilized. As the suspect advances and continues to fire, the officer is forced to quickly utilize the opposite (weak hand) to either recover the weapon or retrieve his/her back-up weapon and accurately return fire in order to neutralize the suspect's attack and save his own life. Possible combat training scenarios are possible as well as the system 10 is mobile and can be used anywhere, inside or outdoors.

Other example uses include high intensity police paint ball training scenarios using 9 mm paint training ammunition; live fire static target drills, involving highly trained units such as SWAT and SEAL teams, etc.; close quarter urban combat training in which police and military use the system 10 for tactical building and room clearing, downed officer extraction, sniper fire on a foot patrol, search warrant entry team drills and rescue drills, police patrol contacts such as pedestrian and traffic stops, surprise shooters, etc.; use with the military Multiple Integrated Laser Engagement Systems (MILES) XXI—the live training system providing realistic training to our ground forces military war games; combat shooting competitions where accuracy and efficiency are critical, such as in the US military's Top Sniper competition in which the system 10 adds a new and extremely realistic element and challenge to the course; private shooting schools that develop "Body Guard Combat Courses" or "Under Fire Survival" courses where certification is achieved after a high level of accuracy is maintained during multiple scenarios and in which certification can be used to add to the private security professional's resume or personal safety development; and paint ball combat course applications. Still other applications include but are not limited to simulating trauma to a fighter, ultimate fight mixed martial arts type fighting. The system 10 may be used to train such fighters to fight with a simulated injured limb and condition them to endure pain and immobility.

Returning to the details of the non-limiting example harness 12 shown in FIG. 1, the harness 12 envelopes at least portions of the trainee's torso, shoulders, and upper legs. Specifically, the harness 12 includes shoulder straps 22a merging into a back center strip 12b, with the receiver assembly 14 being sewn into or otherwise supported by the center strip 12b. A chest strap 12c and waist strap 12d are connected to the shoulder straps 12a, with the waist strap 12d also being connected to the center strip 12b as shown. Opposite ends of the chest strap 12c and waist strap 12d are joined by detachable clips 12e to facilitate donning and removing the harness 12.

Additionally, attached to the shoulder straps 12a are ring-shaped upper and lower elastic armbands 22, one for each of the upper and lower left and right arm as shown. The armbands 22 surround the arms of the trainee and hold leads 16 that are connected to electrodes 18 adhered to the trainee's upper (biceps) and lower (forearms) arms. The armbands may be detachably engaged with the remainder of the harness by a hook-and-eye fastener such as VelCro® to facilitate disposing an electrode lead or leads under them when they are detached and then attaching the armbands to the remainder of the harness to hold the leads against the trainee.

Further, left and right leg strips 24 are attached to and depend down from the waist strap 12d and extend along the back of the trainee's legs to terminate in ring-shaped leg bands 26 which hold leads 16 against the skin, with the leads 16 held by the leg bands 26 being connected to electrodes 18 adhered to the trainee's upper (thighs) and lower (calves) legs. Electrodes 18 may also be adhered to the abdomen of the trainee as shown in FIG. 1. In some embodiments, the leads 16 are wireless leads, i.e., the receiver assembly 14 communicates wirelessly at least in part with the electrodes 18. In this latter case each electrode may be packaged with its own small battery.

In one implementation, the electrodes 18 are disposable electrodes pads that may otherwise be used for EMS Units and that may be physically instantiated by soft, spun-lace cloth electrodes that have conductive solid gel centers and are self-adhering for easy, one-step application. The electrodes may be applied by to the trainee by the trainer to each of the above muscle groups, and then connected to the appropriate leads 16 exiting the wearable harness 12.

Figure 2:
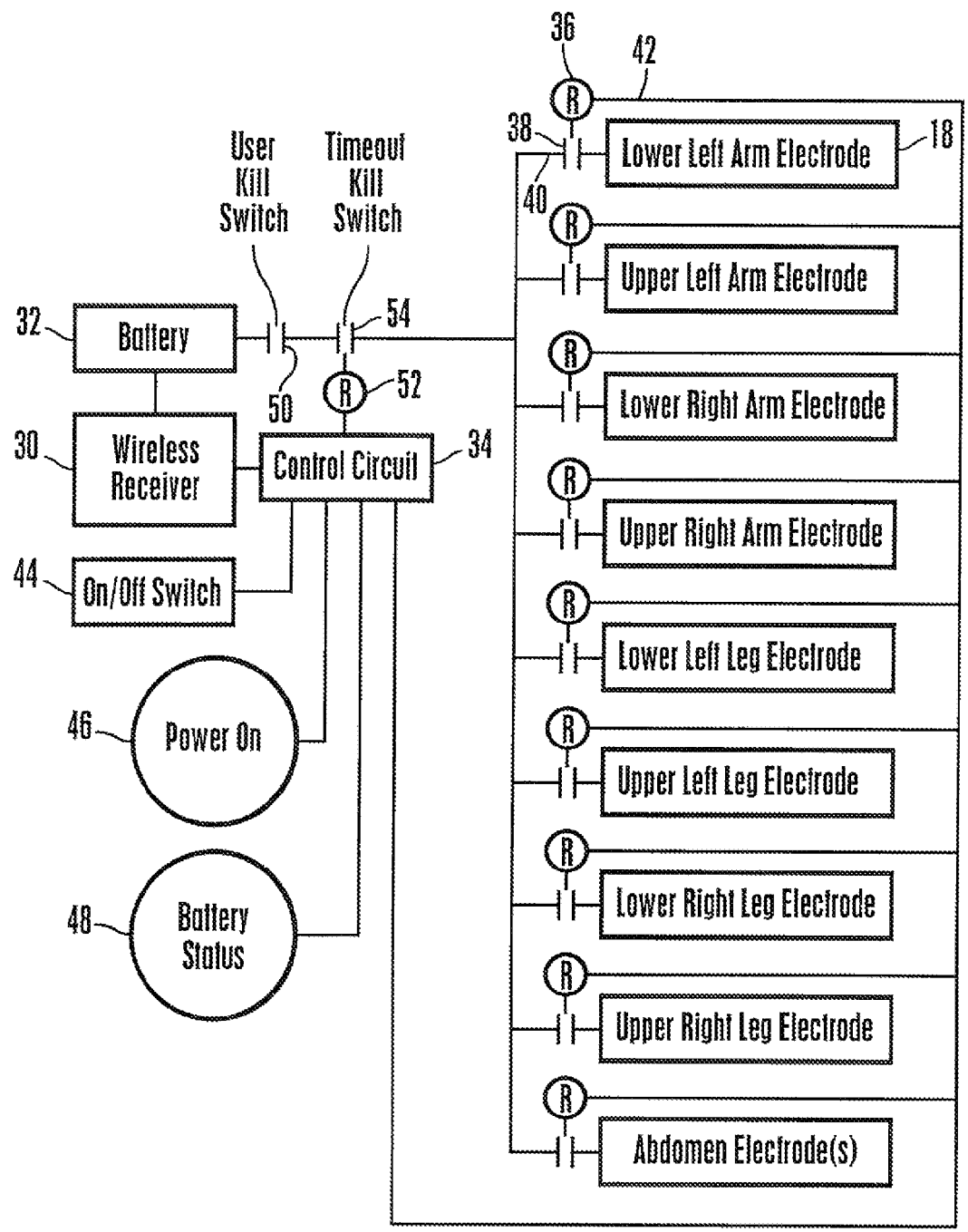
FIG. 2 is a schematic diagram of an example receiver circuit.

Turning now to FIG. 2, a simplified circuit diagram of an example receiver assembly 14 with electrodes 18 may be seen, with appropriate ground connections omitted for clarity. As shown, the receiver assembly 14 can include a wireless receiver 30 powered by one or more rechargeable or primary batteries 32 and controlled by a control circuit 34, which may be implemented by a processor such as but not limited to a programmable gate array or microprocessor. The control circuit 34 can also be powered by the battery 32. The receiver 30 may be a multiple channel nine volt receiver configured to receive a 75 mHz pulse controlled modulation (PCM) signal from the transmitter 20 shown in FIG. 1, although any appropriate frequency may be used, e.g., 27 mHz, 2.4 gHz, etc.

As shown, responsive to signals received by the receiver 30, the control circuit 34 selectively energizes one or a group of relays 36, with each relay 36 closing, when actuated, a respective contact 38. In turn, each contact 38 when shut completes an electrical path between the battery 32 and a respective electrode 18. In the embodiment shown, individual electrodes may be energized for, respectively, contracting the trainee's lower left arm, upper left arm, lower right arm, upper right arm, lower left leg, upper left leg, lower right leg, upper right leg, and abdomen, although when only eight channels are provided one of the arm or leg electrodes may be replaced by the abdomen electrode or the abdomen electrode omitted. Thus, the battery 32 communicates main electrode power to the electrodes 18 through respective main lines 40 while the control circuit communicates control signals to the relays 36 through respective control lines 42, with a lead 16 containing a main line 40 and a control line 42 in some embodiments. In other embodiments, the relays and contacts are housed in the receiver unit worn in the back of the harness in FIG. 1 so that the leads 16 contain only the main lines 40. While FIG. 2 shows that each contact 38 closes to energize a single electrode, each contact 38 may energize multiple closely-spaced electrodes on the same body portion as illustrated in FIG. 1.

The control circuit 34 energizes and deenergizes the receiver assembly 14 responsive to on and off signals from a manually operated switch 44. Also, the control circuit 34 may provide indication of power and battery state by appropriately illuminating power and battery lamps 46, 48, e.g., by turning on the power lamp 46 when power is supplied to the receiver assembly and by illuminating in red the battery lamp 48 when battery voltage falls below a threshold.

As contemplated in some embodiments, the trainee may be given the option of terminating electrode energization regardless of signals being received by the receiver 30, as a safety precaution. To this end, a trainee kill switch is provided which, when actuated as described more fully below, opens a contact 50 between the battery 32 and electrodes 18.

Also, to ensure that the trainee is not subjected to electrode stimulation in the event that the receiver assembly 14 loses communication with the transmitter 20 shown in FIG. 1 or a malfunction occurs, a timeout kill switch is provided. In the event that the control circuit 34 does not receive information from the transmitter 20 for longer than a threshold timeout period (and/or in the event that the control circuit receives unexpected signals indicating transmitter malfunction), the control circuit 34 controls a relay 52 to open a contact 54 between the battery 32 and electrodes 18. Opening either contact 50, 54 may result in only the electrodes 18 being held deenergized or may result in the entire receiver assembly 14 along with the electrodes 18 being deenergized.

Figure 3:
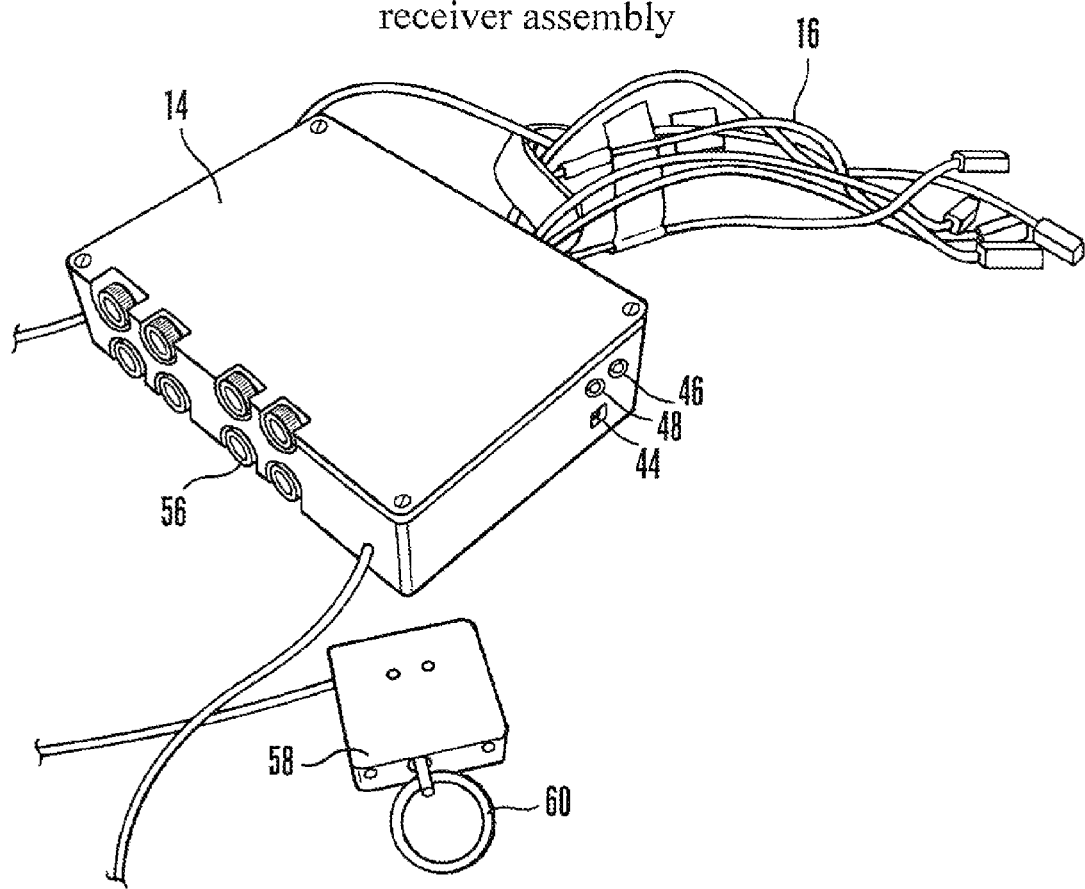
FIG. 3 is a perspective view of an example receiver assembly.

FIG. 3 shows that the receiver assembly 14 may be embodied in a parallelepiped-shaped enclosure with the leads 16 extending therefrom. The on/off switch 44 and indicator lamps 46, 48 are shown embodied as light emitting diodes (LEDs) on the enclosure. Electrode voltage intensity adjustment ports 56 may be provided on some receiver assemblies configured to vary electrode 18 voltage/current, with the voltage/current adjusted for maximum levels for purposes of present principles. A kill switch 58 with trainee-pullable plunger 60 is connected to the receiver assembly to open the contact 50 shown in FIG. 2 when a trainee pulls the plunger 60 out of the kill switch 58.

Details of an example kill switch 58 are shown in FIG. 4. As shown, the plunger 60 is engaged with a lever 62 of the contact 50. Pulling the plunger 60 outward pivots the lever 62, mechanically (and electrically) opening the contact 50.

Details of an example transmitter RC 20 are shown in FIG. 5. In one implementation the RC 20 includes a multiple channel battery-powered twelve volt wireless transmitter housed within a casing 64. The casing 64 can includes an on/off switch 66, a power indicator lamp 68, an antenna, and plural (e.g., eight) keys 70. In the embodiment shown, when a key 70 is manipulated by a trainer, the transmitter RC 20 sends an electrode activation command in a corresponding respective channel which is received by the receiver assembly 14 and correlated to a respective one of the relays 36 shown in FIG. 2 (and, hence, energizing, with constant current, a respective electrode 18 on a respective body portion of the trainee. The associated electrode is energized as long as the trainer depresses a key 70. By pressing one or more keys 70 simultaneously the trainer can target any desired combination of muscle groups for a simulated gunshot hit. When a key 70 is released by the trainer the electrode activation command terminates and the electrode is deenergized. As shown in FIG. 5, each key 70 (not all possible keys shown) may bear the label of the body portion of the trainee that will be stimulated when the key is pressed. Alternate controllers for triggering the electrodes may include a wireless computer, a laser-based controlled, or other signal sending unit.

While the particular PERSONAL UNDER FIRE TRAINER FOR SECURITY AND MILITARY PERSONNEL is herein shown and described in detail, it is to be understood that the subject matter which is encompassed by the present invention is limited only by the claims.

What is claimed is:

1. Training apparatus comprising:
    plural electrodes attachable to respective locations of a body of a patient;
    a harness wearable by the trainee and enveloping at least portions of the trainee's torso, shoulders, and upper thighs;
    at least one battery supported by the harness;
    at least one wireless receiver assembly supported by the harness;
    at least one hand-held controller wirelessly communicating with the wireless receiver assembly and bearing plural keys manipulable by a trainer to send activation signals to the wireless receiver assembly, the wireless receiver assembly responsive to the activation signals causing the battery to activate one or more of the electrodes selectively and thereby cause contraction of at least one muscle of the trainee that is closely juxtaposed with the electrode activated by the battery to simulate a gunshot wound at the site of the electrode activated by the battery; and
    at least one switch electrically disposed between the battery and at least one electrode and operable automatically to open an electrical circuit between the battery and electrode to deactivate the electrode responsive to a determination that the controller is deenergized or malfunctioning.

2. The apparatus of claim 1, wherein the wireless receiver assembly communicates with the electrodes through respective wires connected to respective electrodes, the wires being supported on the harness.

3. The apparatus of claim 1, wherein the wireless receiver assembly wirelessly activates the electrodes.

4. The apparatus of claim 1, wherein each electrode has a conductive gel center supported in a cloth body.

5. The apparatus of claim 1, further comprising at least one trainee-actuated switch electrically disposed between the battery and at least one electrode and operable by the trainee to open an electrical circuit between the battery and electrode to deactivate the electrode in the presence of an activation signal from the controller.

6. The apparatus of claim 1, wherein the switch opens responsive to a determination that the controller is deenergized.

7. The apparatus of claim 6, wherein responsive to the wireless receiver assembly not receiving any signals from the controller for a period of time, a determination that the controller is deenergized is made.

8. Method for stimulating a gunshot wound comprising:
    receiving, at a controller, trainer input of an activate command;
    responsive to the trainer input, wirelessly sending an activate signal to a wireless receiver;
    responsive to receiving the activate signal, causing the receiver to energize at least one electrode contacting a trainee's skin above a muscle to cause the muscle to contract, stimulating a gunshot wound;
    responsive to receiving an emergency stop signal input by the trainee, deenergizing the electrode in the presence of the activate signal; and
    automatically opening an electrical circuit between a source of electrode energy and an electrode to deactivate the electrode responsive to a determination that the controller is deenergized.

9. The method of claim 8, wherein the wireless receiver is supported on a harness worn by the trainee.

10. The method of claim 9, wherein the receiver energizes an electrode through a wire supported in the harness.

11. The method of claim 8, wherein the trainer input is received at a handheld controller bearing plural keys each corresponding to a respective electrode on the trainee.

12. The method of claim 8, wherein the receiver wirelessly energizes an electrode.

13. The method of claim 8, wherein the harness envelopes at least portions of the trainee's torso, shoulders, and upper thighs.

14. A personal under fire trainer, comprising:
- a harness holding a wireless receiver assembly and plural electrode leads;
- the harness being wearable by a trainee with the leads connected to electrodes attached to the trainee's body;
- a controller operable by a trainer to send a wireless signal to the receiver assembly, activating one or more electrodes selectively which contract the trainee's muscles, forcing the trainee to react under simulated gun fight conditions while receiving simulated gunshot wounds;
- at least one battery supported by the harness; and
- at least one switch electrically disposed between the battery and at least one electrode and operable automatically to open an electrical circuit between the battery and electrode to deactivate the electrode responsive to the receiver assembly not receiving any signals from the controller for a period of time, such that responsive to the receiver assembly not receiving any signals from the controller for the period of time, the electrical circuit is opened between the battery and electrode to deactivate the electrode.

15. The trainer of claim 14, further comprising at least one trainee-actuated switch electrically disposed between the battery and at least one electrode and operable by the trainee to open an electrical circuit between the battery and electrode to deactivate the electrode in the presence of an activation signal from the controller.

16. The method of claim 8, wherein responsive to the wireless receiver not receiving any signals from the controller for a period of time, a determination that the controller is deenergized is made.

* * * * *